United States Patent [19]
Wyllie et al.

[11] Patent Number: 5,932,102
[45] Date of Patent: Aug. 3, 1999

[54] IMMOBILIZED METAL, AFFINITY CHROMATOGRAPHY

[75] Inventors: David C. Wyllie, Cranford; John Chu-Tay Tang, Livingston, both of N.J.

[73] Assignee: Schering Corporation, Kenilworth, N.J.

[21] Appl. No.: 09/005,456

[22] Filed: Jan. 12, 1998

[51] Int. Cl.$^6$ ..................................................... B01D 15/08
[52] U.S. Cl. ........................ 210/635; 210/656; 530/413; 530/417
[58] Field of Search ..................................... 210/635, 656, 210/198.2, 659, 502.1; 436/161; 530/412, 413, 416, 417

[56] References Cited

U.S. PATENT DOCUMENTS

| | | | |
|---|---|---|---|
| 4,569,794 | 2/1986 | Smith | 530/413 |
| 4,765,903 | 8/1988 | D'Andrea | 210/635 |
| 5,034,133 | 7/1991 | Naveh | 210/635 |
| 5,047,513 | 9/1991 | Dobeli | 530/412 |
| 5,115,102 | 5/1992 | Haymore | 530/399 |
| 5,136,025 | 8/1992 | Scheurmann | 530/413 |
| 5,169,936 | 12/1992 | Staples | 530/413 |
| 5,372,719 | 12/1994 | Afeyan | 210/656 |
| 5,763,585 | 6/1998 | Nag | 530/413 |
| 5,840,858 | 11/1998 | Smith | 530/413 |

OTHER PUBLICATIONS

Smith et al., 1988, *J. Biol. Chem.* 263(15):7211–15.
Arnold et al., 1991, *Biotechnology* 9:151–56.
Porath et al., 1992, *Protein Expression and Purification* 3:263–81.
Porath et al., 1983, *Affintiy Chromatography and Biological Recognition,* 173–89 (Academic Press, San Diego).

*Primary Examiner*—Ernest G. Therkorn
*Attorney, Agent, or Firm*—J.P. Mc Laughlin

[57] ABSTRACT

A method for purifying protein containing histidine residues using immobilized metal, affinity chromatography. The hydrophilic index of the histidine residues is determined (HI). If the HI is at least 2 the pH of the solution containing the protein is adjusted to about 6.75 to 7.2 and applied to the IMAC column such that the protein binds to the column.

5 Claims, No Drawings

IMMOBILIZED METAL, AFFINITY CHROMATOGRAPHY

BACKGROUND OF THE INVENTION

Immobilized metal affinity chromatography (IMAC), also known as metal chelate affinity chromatography (MCAC), is a specialized aspect of affinity chromatography. The principle behind IMAC lies in the fact that many transition metal ions, i.e., zinc and copper, can coordinate to the amino acids histidine, cystein, and tryptophan via electron donor groups on the amino acid side chains. To utilize this interaction for chromatographic purposes, the metal ion must be immobilized onto an insoluble support. This can be done by attaching a chelating group to the chromatographic matrix. Most importantly, to be useful, the metal of choice must have a higher affinity for the matrix than for the compounds to be purified.

The most common chelating group used in this technique is iminodiacetic acid (IDA). It is coupled to a matrix such as SEPHAROSE 6B, via a long hydrophilic spacer arm. The spacer arm ensures that the chelating metal is fully accessible to all available binding sites on a protein. Another popular chelating group for IMAC applications is tris (carboxymethyl)-ethylenediamine (TED). This particular group lends different properties to the gel than IDA. TED gels show stronger retention of metal ions and weaker retention of proteins relative to that of IDA gels. TED gels form a complex (single coordination site) vs a chelate (multiple coordination sites for IDA gels. The most commonly used metals for IMAC are zinc and copper; however, nickel cobalt, and calcium have also been used successfully.

The develpment of IMAC in purification processes can be facilated considerably by accurate prediction of the protein affinity of a given protein for IMAC resins before performing separations in the laboratory. If the affinity for an IMAC resin could be reliably and easily predicted from its protein structure, then the reseacher would be better informed when deciding on a development strategy. A protein predicted to have a high affinity, for example could be bound to a resin under relatively stringent conditions and eluted with a simple isocratic step. In contrast, IMAC should not be considered as a primary purification step for a protein predicted to possess a low affinity to the metal-chelating resins.

Furthermore, a protein of only moderate affinity requires a less stringent binding condition and a sophisticated gradient elution. To achieve high resolution and maximum recovery in IMAC, however, knowledge of the relative affinity of proteins to immobilized metals is required. Without prediction of protein-resin affinity, purification development of IMAC may become an unnecessarily time consuming effort which may not yield useful results.

Zn-Chelating Chromatography has been utilized in the clinical production of human interleukin-4 (h IL-4), human interleukin-10 (h IL-10) and human tissue plasminogen activator (h tPA). IMAC relies primarily on the interaction between Histidine (His) and a metal ion reversibly bound to a stationery phase. Although immobilized, Zn is extensively used because its selectivity, other metal ions like $Cu^{++}$, $Ni^{++}$, and $Co^{++}$ are also applied for certain proteins. Interactions between immobilized metals and tryptophan, tyrosine, or cysteine residues of proteins have been reported, however, these are generally weaker interactions. Furthermore, when a histidine lies in close proximity to an aromatic residue or another histidine (e.g. on the same position of successive turns of an alpha helix), a cooperative effect leading to high affinity is observed. Although protein leader sequences ontaining His-Tyr, His-Trp, His-X-X-His, have been engineered to take advantage of this phenomenon, these sequences are relatively rare in nature. With naturally occurring proteins, therefore, one can generalize that affinity of a protein for conventional IMAC resins is dictated by the availability of His side chain, imidazole.

Histidine availability, however, is not simply proportional to the total number of His residues in a protein. This is evident from our experience with IMAC of several recombinant proteins under various chromatographic conditions. Since the protein binding capacity of immobilized metal increases as the buffer pH raises, we subjected these proteins to different binding conditions, varied from pH 6.75 (more stringent condition) to pH 7.5 (less stringent condition). Although both h IL-4 and the soluble domain of murine gamma interferon receptor (m IFN R) each contains 5 His residues per monomer, only h IL-4 can bind quantitatively to Zn-Chelating SEPHAROSE under quite stringent conditions (at pH 7.0). In contrast m γIFN R does not significantly bind to the immobilized Zn, either at pH 7.0 or pH 7.7, a more favorable binding condition. A similar phenomenon was observed with h IL-10 and h IL-13. There are 3 His residues per monomer in both of these proteins, but only h IL-10 can bind to the immobilized Zn quantitatively a pH 7.5. Additionally, although the soluble domain of h IL-10 receptor (h IL-10 R) and m γIFN R contain similar numbers of His residues per molecule (7 and 5, respectively), h IL-10 R has remarkably stronger affinity to Zn-Chelating SEPHAROSE. The protein binds quantitatively at pH 6.75, a very stringent condition. This is in contrast to the poor affinity exhibited by m γIFN R, even under the more favorable binding conditions of pH 7.0 and pH 7.5.

These results clearly show that the total number of His residues does not solely determine affinity to IMAC. Therefore, the ability to predict when a His residue is sufficiently exposed to binding to immobilized metals would provide IMAC development with a valuable tool. Thus there is a need to determine a process by which one can determine whether or not a protein will be a suitable candidate for purification by IMAC and what the optimal conditions are.

SUMMARY OF THE INVENTION

The present invention fills this need by providing for a method for purifying a protein contained in a mixture using Immobilized Metal Ion Affinity Chromatography (IMAC). This method is comprised of first sequencing the protein and determine if the protein contains one or more histidine residues, determining the hydrophilicity index (HI) of the histidine residues of said protein, adjusting the pH of the solution to about 6.75 to 7.2 if the HI of the histidine residues is at least 2. The solution is then applied to an IMAC column, so that the protein binds to the column, and eluting the protein from the column.

The present invention is further comprised of a method for removing a contaminant protein from a solution. This method is comprised of sequencing the contaminant protein and determine if the protein contains one or more histidine residues, determining the hydrophilicity index (HI) of the histidine residues of said protein. If the HI of the histidine residues is at least 2, the pH of the solution is adjusted to about 6.75 to 7.2. The solution is the applied to an IMAC column, so that the contaminant protein binds to the column and the effluent is collected which is substantially free of the contaminant protein.

DETAILED DESCRIPTION OF THE INVENTION

The teachings of all references are incorporated herein in their entirety by reference.

Definitions

Hydrophilicity Index

A calculated result that indicates the degree that a residue is hydrophilic. It is based on a sliding window calculation using solvation energy values of individual amino acids, Kyte & Doolittle, *J. Mol. Biol.*, 157: 105–132 (1982).

Surface Probability (SP)

The probability that a residue is on the surface based on the formula of Emini, et al., *J. Virol.*, 55(3), 836–839 (1985), using the empirical amino acid accessible surface probabilities of Janin, et al., *J. Mol. Biol.*, 125: 357–389 (1978).

Antigenic Index (AI)

The probability that a residue is antigenic. It is calculated by summing several weighted measures of secondary structures [Jameson and Wolf, *CABIOS*, 4(1), 181–186 (1988)].

Solvent-exposed Surface Area (SESA)

This property is calculated by molecular modeling, using software such as Delphi and Solvation (MSI). Several isomers representing the most probable forms of the protein at the pH range of interest are generated using DISCOVER (MSI) and programs to calculate the pKa's of amino acid side chains (Yang et al., 1994 and Antosiewicz et al., 1995). The isomers analyzed for exposure of individual imidazole nitrogens and hyudrogens, using Delphi and Solvation (MSI).

To determine the hydrophilicity index (HI) of the exposed His imidazole nitrogens, we have employed the 'Peptidstructure'(Version 8.0) computer program, Genetics Computer Group, Inc., for secondary structure prediction. All of the default settings were used, except that the 'word size' setting for the calculation was 7, the default for KD. The remaining manipulations (i.e. making charts) were performed using the program Excel, Lotus Inc. An alternative program is the 'General Protein/Mass Analysis for Windows', Lighthouse Data. In general, these algorithms use a 'sliding window' approach in which each residue of the sequence is measured together with adjacent residues for a property. By accounting for the effects of neighbors in linear sequence, these algorithms predict the location of hydrophilic or hydrophobic patches in a protein. Several computer-based algorithms have been developed to predict the related properties of hydrophilicity and surface probability from the primary structure of proteins. Since hydrophilic areas tend to be located on the surface of molecules, a hydrophic histidine residue is probably more accessible to the immobilized metal during IMAC.

Using the Kyte-Doolittle sliding window algorithm of the example discuess above, we found that the 5 histidine residues of h IL-4 have predicted hydrophilic indices (HI) of 2.03, 1.87, 2.77, 2.71 and 1.67 respectively (all above 1.5). While the values for m γIFN R are notably lower at 0.71, 0.71, 0.39, −0.34 and −1.04, respectively (all below 0.75). Thus the predicted HI values correlate with the experimental results: only the protein that contained significantly hydrophilic histidine residues (h IL-4 but not m γIFN R) showed high affinity to the immobilized metal.

We further analyzed the predicted hydrophilicity of histidine residues in other recombinant proteins, including h IL-10, h IL-4R, h IL-10 R, h γIFN, h IL-13, human granulocyte macrophage-colony stimulating factor (h GM-CSF) and h tPA. These HI predictions were then compared with their binding characteristics to immobilized Zn resins (Table 1). These results showed that there is a clear correlation between the number of hydrophilic histidine residues in a protein and its relative affinity for immobilized Zn resins. By analyzing the binding characteristics and HI figures for 9 proteins, we have been able to define the following HI Thresholds.

1. All proteins that contain histidine residues with a predicted HI greater than 1.0, e.g. h IL-4, h IL-10, h IL-4 R, h IL-10 R, h γIFN, h IL-13, h GM-CSF, and h tPA, show moderate to high affinity for IMAC resins and invariably bind to the immobilized Za at pH 7.5.
2. Most proteins that possess any histidine residues with a predicted HI greater than 2.0, such as h IL-4, h IL-10 R, h IL-4-R and h tPA, show high affinity for IMAC resins, as evidenced by their ability to bind to Zinc-Celating SEPHAROSE at pH 7.0.
3. Proteins with a predicted HI of less than 1.0, such as h IL-13 and m γIFN R, for example, demonstrate low affinity for IMAC resins. Even at pH 7.7, these proteins do not bind quantitatively to Zinc-Chelating SEPHAROSE.

The idea of predicting IMAC affinity through computer-based structure analysis is enhanced by the more sophisticated tools of molecular modeling. The Solvent-Exposed Surface Area (SESA) of imidazole nitrogens can be calculated when the tertiary structure is known. These precise calculations of SESA from molecular modeling are relatively simple and generate a greater degree of confidence in IMAC affinity predictions. In the case of h IL-4, two histidine imidazolyl nitrogens (NE2 atoms) have high SESA (greater than 3.5 square Angstroms), which is consistent with its high affinity for immobilized metals. In contrast, NE2 atoms in h IL-10, which possesses moderate affinity for IMAC, have a low SESA (less than 2.5 square Angstroms) to the solvent.

These correlations demonstrate that the affinity of proteins to immobilized metals can be confidently predicted from primary sequence or tertiary structure of proteins. Therefore, such predictions provide valuable data to allow informed strategy design when evaluating IMAC as a potential purification tool. Although our model is based on results derived from Zn-Chelating Chromatography, the relative affinity of a large group of proteins to other immobilized metals, $Cu^{++}$, $Ni^{++}$ and $Co^{++}$, for example, can be predicted similarly because they are all involved in the same type of interactions.

Based on predicted Hydrophilic Indices and/or Solvent Exposed Surface Area of imidazole nitrogens, one can determine strategies for efficient IMAC development as follows.

1. High Affinity Proteins with HIS of Predicted HI>2.0 and/or SESA<3.5 (Å)$^2$
   a. To consider IMAC for the first step of purification;
   b. To use more stringent conditions for removing most impurities present in the starting materials;
   c. To recover proteins with a mild and simple elution from the column.
2. Moderate Affinity Proteins with HIS of 1.0<Predicted HI<2.0
   a. To consider IMAC for the early step of purification;
   b. To use less stringent conditions for maximizing binding;

c. To develop an optimized gradient elution for separating other impurities bound to the column.
3. Low Affinity Proteins with HIS of Predicted HI<1.0
   a. Not to be considered for primary purification step;
   b. To be used only in the late step of the purification, and possibly use in a flow-thru mode to remove proteins with high affinity to the IMAC resins.

and 4 histidine residues having an HI value less than one. The stationary phase was Zinc-chelating Fast Flow Sepharose. The equilibration and wash buffer was 20 mM sodium phosphate, 100 mM sodium acetate, 500 mM NaCl, pH 7.2. The protein solution, a Q Sepharose pool from CHO cell culture supermatant, was adjusted to pH 7.2 and 50–55 mS before loading. Isocratic elution was accomplished with Summary of IMAC Results Using Zinc as the Stationary Phase

| Protein | Nature of Feed | Step in Process | Loading pH | Eluting pH | Result |
|---|---|---|---|---|---|
| h IL-4 | Secrectary E. coli fermenation broth | First | 6.75 | 5.5 | Recovered in eluate. Slight loss in flow-thru and wash. |
| | | | 7.2 | 5.5 | Recovered in eluate with high yield. |
| | | | 7.5 | 5.5 | Recovered in eluate with high yield. |
| h IL-10 | Q-Sepharose Pool from CHO cell culture supermatant | Third | 7.2 | 5.5 | Poor recovery in eluate. Some loss in flow-thru and wash. |
| h IL-13 | Q-Sepharose Pool from E. coli | Second | 7.0 | 5.0 | Very poor recovery in eluate. Major loss in flow-thru and wash. |
| | | | 7.2 | 5.0 | Poor recovery in eluate. Significant loss in flow-thru and wash. |
| | | | 7.5 | 6.5* | Poor recovery in eluate. Significant loss in flow-thru and wash. |
| h IL-4-receptor | m melanoma (NS-0) cell cultured supermatant | First | 7.2 | 6.5* | Recovered in eluate with some loss in flow-thru or wash. |
| h IL-10-receptor | m melanoma (NS-0) cell cultured supermatant | First | 6.75 | 6.5* | Recovered in eluate with some loss in flow-thru or wash |
| h γ-interferon-receptor | Secretory E. coli fermenation broth | First | 7.2 | 5.0 | Major loss in flow-thru. Very low recovery in eluate. |
| | | | 7.7 | 5.0 | Major loss in flow-thru. Very low recovery in eluate. |
| h GM-CSF | NA | NA | NA | NA | NA |
| h TPA | h melanoma (Bowes) cell culture supermatant | First | 7.5 | 7.5* | Recovered in eluate with high yield |

Eluting conditions marked with an asterisk used a gradient elutioin with imidazole. All others elutions were performed by step elution with 50 mM sodium acetate.

Human Interlukeukin 4

IL-4 has 129 total amino acids 5 histidine residues, 3 of which have an HI value less than two but greater than one and 2 histidine residues having an HI value greater than two. The stationary phase was Zinc-chelating Fast Flow Sepharose. The equilibration and wash buffer was 20 mM sodium phosphate, 100 mM sodium acetate, 500 mM NaCl, pH 6.75, 7.0, 7.2, or 7.5. The protein solution, a crude E.coli fermentation broth was adjusted to match the wash buffer. Isocratic elution was accomplished with 20 mM sodium phosphate, 100 mM sodium acetate, 500 mM NaCl, pH 5.5.

This protein was very effectively purified from a crude E.coli broth at several pH conditions. When located onto Zinc-chelating Sepharose at pH 7.0, 7.2, or 7.5 and above, the protein was quantatitively recovered (>85%) in the eluate, with no detectable amounts lost in the flow-through, wash, or post-elution strip. At pH 6.75, ~80–85% of the hIL4 was recovered in the eluate.

Human Interleukin 10

IL-10 has 158 total amino acids 6 histidine residues, 2 of which have an HI value less than two but greater than one 20 mM sodium phosphate, 100 mM sodium acetate, 500 mM NaCl, pH 5.5.

IL10 was applied to Zinc-chelating Sepharose at pH 7.2. Recovery in the eluate was ~45% by ELISA. A dilute amount of hIL10, which could be observed by Western blot but was below the sensitivity threshold of ELISA assays, was present in the flow-through. Resolution from other proteins was poor. Only a relatively small amount, ~10–20%, of host-derived protein was removed in the flow-through.

Human Interlleukin 13

IL-13 has 111 total amino acids, 3 histidine residues which have an HI value less than one. The stationary phase was Zinc-chelating Fast Flow Sepharose. The equilibration and wash buffer was 20 mM sodium phosphate, 1M NaCl, pH 7.0, 7.2, 7.5. The protein solution, a Q Sepharose pool from E.coli fermentation broth, was adjusted to pH 7.0, 7.2 or 7.5 and 61 mS before loading. Isocratic elution was accomplished with 20 mM sodium phosphate, 10 mM sodium acetate, 500 mM NaCl, pH 5.

IL13 did not exhibit high affinity to Zinc-chelating Sepharose. When a relativity pure preparation (>80% hIL13)

was applied to the resin at either pH 7.0 or 7.2 and eluted isocratically with sodium acetate, pH 5.5, only 7% or 30%, respectively (by UV absorbance) was recovered in the eluate, with the remainder lost in the flow-through and wash fractions. When the preparation was applied at pH 7.5 and eluted with an imidazole gradient, the recovery was similar to the pH 7.2 separation, but the purity appeared significantly improved to >90%.

Human Interleukin 4 Receptor (Soluble Domain)

The soluble domain of the human IL-4 receptor has 207 total amino acids, 7 histidine residues, 2 of which have an HI value less than two but greater than one, 4 histidine residues having an HI value less than one and 1 histidine residue having an HI value greater than two. The stationary phase was Nickel-chelating Fast Flow Sepharose. The equilibration and wash buffer was 20 mM sodium phosphate, 1M NaCl, pH 7.2. The protein solution, a crude cell culture supermatant from murine melanoma (NS-0) cells, was adjusted to match the wash buffer. Gradient elution was accomplished in 10 column volumes with 20 mM sodium phosphate, 20 mM sodium imidazole, 500 mM NaCl, pH 6.5.

When a crude preparation from a murine melanoma cell culture supermatant was applied at pH 7.2, only 9% was lost in the flow-through and wash. The remainder was eluted by a gradient with imidazole.

Human Interleukin 10 Receptor (Soluble Domain)

The soluble domain of the human interleukin-10 receptor has 219 total amino acids, 10 histidine residues, 3 of which have an HI value less than two but greater than one, 6 histidine residues having an HI value less than one and 1 histidine residue having an HI value greater than two. The stationary phase was Nickel-chelating Fast Flow Sepharose. The equilibration and wash buffer was 20 mM sodium phosphate, 1M NaCl, pH 7.2. The protein solution, a crude cell culture supernatant from murine melanoma (NS-0) cells, was adjusted to match the wash buffer. Gradient elution was accomplished in 10 column volumes to with 20 mM sodium phosphate, 20 mM sodium imidazole, 500 mM NaCl, pH 6.5.

When a crude preparation from a murine melanoma cell culture supernatant was applied a pH 6.75, recovery appeared to be quantitative, with no loss of material was observed by Western blot in the flow-through or wash.

Human Gamma-Interferon Receptor

The soluble domain of the human gamma-interferon receptor has 227 amino acid residues, 5 histidines all of which have an HI value less than 1. The stationary phase was Zinc-chelating Fast Flow Sepharose. The equilibration and wash buffer was 20 mM soium phosphate, 100 mM sodium acetate, 500 mM NaCl, pH 7.2 or 7.7. The protein solution, crude E.coli fermentation broth was adjusted to match the wash buffer. Step elution was accomplished with 20 mM sodium phosphate, 100 mM sodium acetate, 500mM NaCl, pH 5.5.

This soluble receptor domain exhibited remarkably low affinity toward Zinc-chelating Sepharose. When applied at either pH 7.2 or 7.7, over 85% was lost in the flow-through and wash.

Human Tissue Plasminogen Activator

Human Tissue Plasminogen Activator has 530 total amino acids, 16 histidine residues, 1 of which have an HI value less than two but greater than one, 14 histidine residues having an HI value less than one and 1 histidine residue having an HI value greater than two. The stationary phase was Zinc-chelating Fast Flow Sepharose. The equilibration and wash buffer was 20 mM sodium phosphate, 100 mM sodium acetate, 500 mM NaCl, 0.01% Tween 80, pH 7.5. The protein solution, a crude cell culture supernatant from human melanoma (Bowes) cells, was adjusted to match the wash buffer. Gradient elution was accomplished with 0–50 mM imidazole in equilibration buffer.

When loaded onto Zinc-chelating Sepharose at pH 7.5, the protein was quantatitively recovered (>85%) in the eluate with no loss detected by Western in the flow-through or wash.

We claim:

1. A method for purifying a protein contained in a solution using Immobilized Metal Ion Affinity Chromatography (IMAC) comprising:
    (a) sequencing the protein and determine if the protein contains one or more histidine residues;
    (b) determining the hydrophilicity index (HI) and/or the Solvent-Exposed Surface Area (SESA) of the histidine residues of said protein;
    (c) adjusting the pH of the solution to about 6.75 to 7.2 if the HI of at least one of the histidine residues is at least 2 and/or the SESA of at least one histidine residue of the protein is at least about 3.5 $(Å)^2$;
    (c) applying the solution to an IMAC column, so that the protein binds to the column; and
    (d) eluting the protein from the column.

2. The method of claim 1 wherein the pH of the solution is adjusted to a pH of between 7.2 and 8.0 in step (c) if none of the histidine residues of the protein have an HI of at least 2, and at least one of the histidine residues has an HI of less than 2 and greater than 1.

3. A method for removing a contaminant protein from a solution comprising:
    (a) sequencing the contaminant protein and determine if the protein contains one or more histidine residues;
    (b) determining the hydrophilicity index (HI) and/or the Solvent-Exposed Surface Area (SESA) of the histidine residues of said protein;
    (c) adjusting the pH of the solution to about 6.75 to 7.2 if the HI of at least one of the histidine residues of the protein is at least 2 and/or the SESA of at least one histidine residue of the protein is at least about 3.5 $(Å)^2$;
    (d) applying the solution to an IMAC column, so that the contaminant protein binds to the column; and
    (e) collecting the resultant effluent which is substantially free of the contaminant protein.

4. The method of claim 3 wherein the pH of the solution is adjusted to a pH of between 7.2 and 8.0 in step (c) if none of the histidine residues of the protein have an HI of at least 2, and at least one of the histidine residues has an HI of less than 2 and greater than 1.

5. A method for purifying a protein contained in a solution using Immobilized Metal Ion Affinity Chromatography (IMAC) comprising:
    (a) sequencing the protein and determine if the protein contains one or more histidine residues;
    (b) determining the hydrophilicity index (HI) of the histidine residues of said protein;
    (c) adjusting the pH of the solution to less than 8.0 if the HI of none of the histidine residues is at least greater than one;
    (c) applying the solution to an IMAC column, so that the protein does not bind to the column; and
    (d) collecting the resultant flow-through fraction containing the protein.

* * * * *